United States Patent [19]

Kesten et al.

[11] Patent Number: 4,478,814

[45] Date of Patent: Oct. 23, 1984

[54] GAS TRANSPORTING SYSTEM

[75] Inventors: Arthur S. Kesten, West Hartford; Harold T. Couch, Columbia, both of Conn.

[73] Assignee: United Technologies Corporation, Hartford, Conn.

[21] Appl. No.: 431,495

[22] Filed: Sep. 30, 1982

[51] Int. Cl.³ .............................................. C01B 13/00
[52] U.S. Cl. .................................. 423/650; 422/189; 423/648 R; 423/652; 423/659
[58] Field of Search .................... 423/648 R, 650, 652, 423/659

[56] References Cited
U.S. PATENT DOCUMENTS 3,690,550  9/1972  Hilberath et al. ..................... 48/190
4,346,752  8/1982  Kesten et al. .................. 165/104.12

Primary Examiner—John Doll
Assistant Examiner—Wayne A. Langel
Attorney, Agent, or Firm—Stephen E. Revis

[57] ABSTRACT

A first gas produced or supplied at a first location is reacted (combined) with a selected reactant in a reversible chemical reaction to produce a gaseous reaction product which is converted to liquid-form and conveyed, as a liquid, to a second location remote from the first location, whereupon it is converted back to its original gaseous constituents in a chemical reaction the reverse of the initial reaction. The regenerated first gas, now at the second location, is separated from the regenerated reactant which is returned to the first location to be used again.

6 Claims, 2 Drawing Figures

GAS TRANSPORTING SYSTEM

DESCRIPTION

1. Technical Field

The present invention relates to a method and apparatus for transporting a gas over relatively long distances.

2. Background Art

Chemical heat pipes involving reversible endothermic/exothermic chemical reactions are well known in the art for efficiently transporting thermal energy between a heat source and a heat sink which are separated from each other by a relatively long distance. In such a chemical heat pipe system, a reactant or reactants within the system undergo a first chemical reaction at the heat source and a second chemical reaction at the heat sink. The first chemical reaction is of an endothermic nature in which heat is chemically absorbed by the reaction process, and the second reaction is an exothermic reaction during which heat is chemically liberated during the reaction process. These chemical reactions are reversible and are effected and/or accelerated by a catalyst at one or both of the reaction sites. Since the purpose of chemical heat pipes is to transfer heat, it is most preferred, if not actually necessary, that a large heat source be available at the endothermic reaction site and a large heat sink be available at the exothermic reaction site.

A variety of reactants have been used in chemical heat pipe systems, including cyclohexane and/or methylcyclohexane. Methane is used in U.S. Pat. No. 3,690,550, and is reformed, with the addition of heat, to the reaction products hydrogen, carbon monoxide, and carbon dioxide. These reaction products are transported through a leg of a closed circuit flow path to a heat sink position where methanization takes place and the heat added during reforming is released. The methane produced is returned to the reformer at the heat source position through a second leg of the closed circuit flow path. If the methane produced by the methanization reaction is used for chemical reactions, a corresponding quantity of methane from another source is added to the second leg.

Typically, one or more pumps and/or blowers are provided in the system's flow path for effecting the requisite reactant transport; however, in commonly owned U.S. Pat. No. 4,346,752 a self-driven chemical heat pipe system is described which eliminates the need for such pumps or blowers. A number of other prior art patents relating to chemical heat pipes are cited and discussed in that patent.

DISCLOSURE OF INVENTION

The primary object of the present invention is to efficiently transport a gas produced at a first location to a use site at a second location remote from the first location.

In accordance with the present invention, a supply of a first gas at a first location is transported to a second location remote therefrom by introducing it near the first location into the flow path of a reversible chemical reaction system as one of the reactants; reacting the first gas, in a first reaction, with another reactant at a gas association position in the flow path to produce a gaseous reaction product which is converted to liquid-form and transported, as a liquid, to a gas regeneration position in the flow path; regenerating the reactants in a second reaction, the reverse of said first reaction, at the gas regeneration position; removing at least a portion of the regenerated first reactant gas from the flow path near the second location; and conveying the remaining reactants back to the gas association position to react with a new supply of first reactant gas.

Prior art methods for transporting gases over long distances are relatively inefficient in view of the great volume of gas which must be moved even after compressing the gas, which requires considerable energy per unit mass of gas. In the present invention the gas to be transported is, in essence, converted to liquid-form, transported as a liquid, and then reconverted back to its original gaseous state. The transformation from gas to liquid, back to gas, involves, as its principal step, a reversible chemical reaction within a flow path loop. Transporting the gas in the form of a liquid has, as a major advantage, the elimination of the need to compress the gas; and, further, it significantly reduces both the size of the conduit needed for the transport and the energy required for transport. A further advantage of using a reversible chemical reaction as part of the process to convert the gas to a liquid form, is that the energy used to regenerate the gas in the regeneration reaction is or may be substantially completely recovered during the combination reaction. In one embodiment of the present invention the fluids within the flow path loop are self-driven, which further increases efficiency.

In a preferred embodiment hydrogen is the gas to be transported. It may be produced in a steam reform reactor, coal gasifier, or the like, and introduced into a nearby first reaction chamber in the flow path loop of a chemical heat pipe along with a reactant such as toluene which exothermically reacts with the hydrogen to produce gaseous methylcyclohexane. The gaseous methylcyclohexane is condensed to a liquid which is conveyed through the flow path loop to a second reaction chamber remote from the first reaction chamber and near the final destination of the hydrogen. In the second reaction chamber the methylcyclohexane goes through an endothermic dehydrogenation reaction to regenerate hydrogen and toluene gas. The hydrogen gas, or a portion of it, is separated from the toluene and removed from the flow path loop at a point near its final destination, to be used as desired. The toluene and any remaining hydrogen are returned to the first reaction chamber in the flow path loop to react with each other and with newly supplied hydrogen.

The foregoing and other objects, features and advantages of the present invention will become more apparent in the light of the following detailed description of preferred embodiments thereof as shown in the accompanying drawing.

BEST MODE FOR CARRYING OUT THE INVENTION

Figure 1:
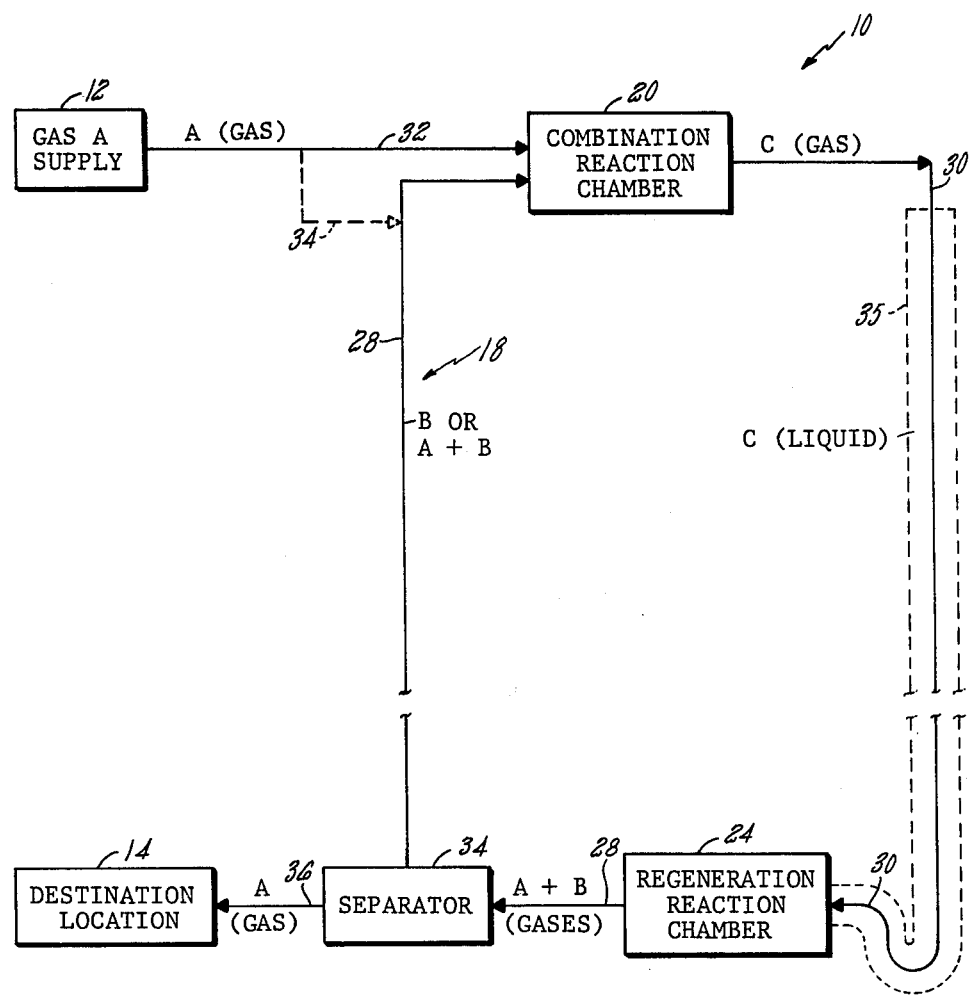
FIG. 1 is a schematic representation of a gas transporting system according to the present invention.

Referring to FIG. 1 there is schematically illustrated a gas transport system generally represented by the numeral 10. In this system 10 a supply 12 of gas A is transported to a distant destination location 14 using, in part, reversible chemical reactions which have heretofore only been used in chemical heat pipe systems to transport thermal energy between a heat source and heat sink.

More specifically, the transport system 10 includes a flow path loop 18. Within the flow path loop is a first reaction chamber 20 and a second reaction chamber 24. A first leg 28 of the flow path loop 18 connects the second reaction chamber outlet with the first reaction chamber inlet; and a separate second leg 30 of the flow path loop 18 connects the first reaction chamber outlet to the second reaction chamber inlet. Gas A from the supply 12 (hereinafter referred to as reactant A) is conveyed via a conduit 32 into the first reaction chamber 20, along with a reactant B from the first leg 28 of the flow path loop. Relative to the distance between the supply 12 and destination location 14, the supply 12 and the first reaction chamber 20 are near each other. (As suggested by the dotted line 34, reactant A could also be introduced into the first leg 28 upstream of the reaction chamber 20 such that it is premixed with reactant B as it enters the reaction chamber 20.)

Within the reaction chamber 20 reactant A and reactant B undergo a reversible chemical combination reaction to form a gaseous reaction product C. (Hereinafter, the reaction chamber 20 is considered to be located at the combination position of the flow path loop.) Gaseous reactant C is then converted to liquid-form, such as by passing it through a condenser or dissolving it in a suitable liquid. The liquid-form reaction product C (within the portion of the second leg 30 enclosed by the phantom line 35) is conveyed through the second leg 30 of the flow path loop 18 into the second reaction chamber 24. In the reaction chamber 24 the reaction product C vaporizes and then undergoes a chemical reaction the reverse of the reaction in the chamber 20, to regenerate the reactant gases A and B. (Hereinafter, the reaction chamber 24 is considered to be located at the regeneration position of the flow path loop.)

Some or all of the regenerated reactant gas A is separated from reactant B in a separator 34 and is removed from the flow path loop 18 via a conduit 36, which conveys it to the nearby destination location 14. The reactants A and B remaining in the flow path loop 18 (or only reactant B if all of reactant A has been removed) are returned to the first reaction chamber 20 via the first leg of the flow path loop 18 to complete the cycle. The separator 34 may, for example, be a condenser, wherein reactant gas B is converted to a liquid and reactant gas A remains a gas and is removed from the flow path loop 18 as a gas. Reactant B in liquid form is then conveyed back to the first reaction chamber 20 via the first leg 28 of the flow path loop 18. Pumps or gravity are used to circulate the liquids around the flow path loop 18.

In the transport system 10 of the present invention, reactant A from the supply 12 is introduced into the flow path loop at a first location which will generally be near or at the flow path loop combination position; and reactant A is removed from the flow path loop 18 at a location in the second leg 28 of the flow path loop upstream of the first location and generally near the regeneration position of the flow path loop. The distance between the entry and removal locations of reactant A is, therefore, substantially the distance separating the gas supply 12 and the destination location 14. The reactant A traverses essentially that distance as a constituent or component of the liquid reaction product C.

As pointed out in the Background Art portion of this specification, prior art chemical heat pipe systems for transporting thermal energy need to use reversible chemical reactions requiring, at one end, a large input of thermal energy, and, at the other end, a large outflow of thermal energy. That is not the case with the present invention. The amount of thermal energy transferred in the system of the present invention, if any, is not related to the system's ability to transport gas between remote locations. For example, any energy transferred from an endothermic reaction at the regeneration position of the flow path loop to an exothermic reaction at the combination position could be thrown away without affecting gas transport (albeit, it would be wasteful and might make the system economically unattractive). Thus, the important aspect of the chemical reactions of the present system is their reversibility and not whether and to what extent they are exothermic or endothermic.

Figure 2:
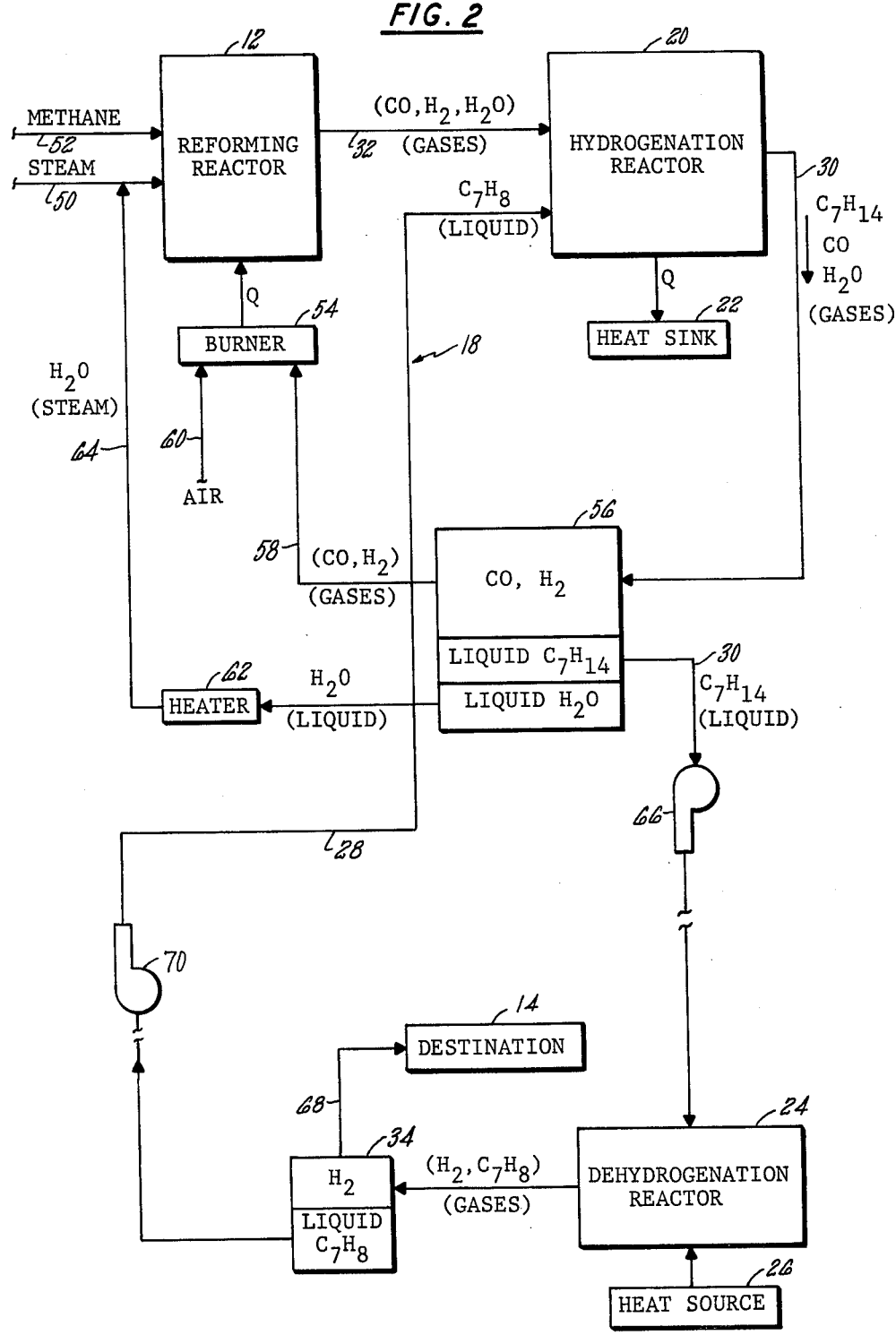
FIG. 2 is a schematic representation of an exemplary embodiment of a gas transporting system according to the present invention.

Referring to FIG. 2, components analogous to those of the system of FIG. 1 have been given the same reference numerals. In the embodiment of FIG. 2, the reactant A is hydrogen, the reactant B is toluene, and the reaction product C is methylcyclohexane. The hydrogen is supplied by a steam reforming reactor 12 which is fed steam via a conduit 50 and methane (or natural gas which is mostly methane) via a conduit 52. Heat is supplied to the reactor 12 by a burner 54. Within the reactor 12 methane reacts with water (steam) in the presence of a catalyst to produce carbon monoxide and hydrogen in accordance with the following equation:

$$CH_4 + H_2O \rightarrow CO + 3H_2 \tag{1}$$

The carbon monoxide and hydrogen, as well as some unreacted water vapor, is conveyed from the reactor 12 into the first reaction chamber 20 via a conduit 32. Toluene from the first leg 28 of the flow path loop 18 is also fed into the combination reaction chamber 20. In this embodiment the combination reaction chamber 20 is a hydrogenation reactor. Liquid toluene entering the reaction chamber 20 is vaporized by mixing with the hot gases exiting from the reactor 12 and by heat generated during the hydrogenation reaction. Vaporized toluene selectively reacts with the hydrogen exothermically within the reaction chamber 20 to produce gaseous methylcyclohexane plus heat in accordance with the following equation:

$$C_7H_8 + 3H_2 \rightarrow C_7H_{14} + Q \tag{2}$$

During the reaction the heat is released to a heat sink 22 and is preferably used elsewhere in the system.

The gaseous reaction product methylcyclohexane, as well as some water (steam), carbon monoxide, and perhaps some unreacted hydrogen pass from the reaction chamber 20 into the second leg 30 of the flow path loop 18. These gases are passed through a condenser/separator 56 which converts the methylcyclohexane and the steam to liquids which are immiscible and therefore easily separated. The carbon monoxide and excess hydrogen are conveyed to the burner 54 of the reactor 12 via a conduit 58 and are used as the fuel therefor or to supplement a separate fuel supply. Air is shown being provided to the burner via a conduit 60. The liquid water is reconverted to steam by passing it through a heater 62 and is introduced into the steam supply conduit 50 via a conduit 64, for use in the reactor 12.

The liquid methylcyclohexane remains in the leg 30 of the flow path loop 18 and is conveyed to the second reaction chamber 24 in the flow path loop 18 via a pump 66 (or by gravity, if possible). The second reaction chamber 24 is a dehydrogenation reactor. The methylcyclohexane, which may enter the reaction chamber 16 in a liquid state, is vaporized by a heat source 26 at high temperature, generally in excess of 600° F. at atmospheric pressure. Further heat is added to the vaporized reaction product by the heat source 26, which product then reacts endothermically and dissociates or dehydrogenates into hydrogen and toluene in the gaseous state according to the following equation, which is the reverse of equation (2):

$$C_7H_{14} + Q \rightarrow C_7H_8 + 3H_2 \tag{3}$$

Thus, the original reactants entering the first reaction chamber 20 are regenerated in the second reaction chamber 24. The amount of thermal energy required for the dehydrogenation reaction is substantially the same as the amount of thermal energy released to the heat sink 22 during the hydrogenation reaction.

The gaseous reaction products from the second reacton chamber 24 at the regeneration position of the flow path loop 18 leave the reactor 24 and enter the first leg 28 of the flow path loop 18. These products are passed through a separator 34 within the first leg 28. The separator 34, in this instance, is a condenser which reduces the temperature of the gaseous reactants sufficiently to convert the toluene to a liquid. The separated hydrogen gas is removed from the flow path loop 18 via a conduit 68 and conveyed to its destination location 14 for either immediate use or storage. The liquid toluene is returned to the reaction chamber 20 by means of gravity or a pump 70 within the first leg 28 of the flow path loop 18 to complete the cycle.

The transport system of FIG. 2 is particularly well suited to distributing hydrogen from a single hydrogen production facility to a number of widely dispersed user sites remote from the facility, such as fuel cell power plants which use hydrogen for fuel.

As is apparent from the exemplary embodiment of FIG. 2, the present invention does not require an initially pure supply of the gas which is to be transported (i.e., the primary gas), as long as the second reactant selectively reacts with the primary gas to produce a reaction product which may be converted to a liquid and separated from any undesirable constituents which may be mixed with the reaction product when it leaves the combination reaction chamber. Thus, although in FIG. 2 the hydrogen is produced by steam reforming a light hydrocarbon fuel, the present invention is not limited to such reaction. For example, the hydrogen may be produced by the gasification of coal.

The transport system 10 of FIG. 2 may be modified to take advantage of the teachings of hereinabove referred to U.S. Pat. No. 4,346,752, incorporated herein by reference, which is a chemical heat pipe system wherein the circulating fluids are self-driven. In the self-driven heat pipe system described in that patent the gaseous dehydrogenation products hydrogen and toluene are regenerated at a first pressure by an endothermic reaction in a reaction chamber at a heat source position of the flow path loop; and both gases are conveyed, via the first leg of the flow path loop into a reaction chamber at a heat sink position of the flow path loop in which they react exothermically to create gaseous methylcyclohexane at a pressure less than the first pressure. The gaseous methylcyclohexane is converted to liquid-form, which liquid-form fully occludes part of the second leg of the flow path loop and provides a mechanism for transport of the methylcyclohexane toward the heat source position of the flow path loop. The second leg of the flow path loop ends at the heat source position and is in the form of a U-shaped liquid trap which prevents gases within the reaction chamber at the heat source position from flowing backward into the second leg of the flow path loop. The pressure differential which exists within the flow path loop drives the gases produced at the heat source position through the first leg toward the heat sink position. A further description of the self-driven heat pipe system may be had by referring to the patent.

The transport system of FIG. 2 uses the same reactants used in the self-driven heat pipe system described in U.S. Pat. No. 4,346,752, namely, hydrogen and toluene; and, therefore, may be readily modified to operate as a self-driven system. For example, the separator 34 may be a selective membrane, such as a palladium membrane which selectively passes hydrogen gas. The downstream end of the second leg 30 of the flow path loop 18 would be in the form of a U-shaped liquid trap where it enters the second reaction chamber. This prevents backflow of gases and assures that at least a portion of the second leg is fully occluded by the liquid reaction product such that the pressure needed for self-driving the system may build up. Only a portion of the hydrogen gas would be removed from the flow path loop at the separator 34 so as not to reduce the pressure of the gaseous mixture to below that of the gaseous methylcyclohexane produced in the first reaction chamber 20. The mixture of hydrogen and toluene gas remaining in the flow path loop 18 travels through the first leg 28 into reaction chamber 20 as a result of the pressure differential; and hydrogen from the reactor 12, in quantities at least as great as the amount removed at the separator 34, is also introduced into the reaction chamber 20. With those modifications the pumps 66 and 70 are not required since the pressure gradient within the flow path loop 18 cause the fluids therein to flow in the proper direction without mechanical assistance.

Although the invention has been shown and described with respect to a preferred embodiment thereof, it should be understood by those skilled in the art that other various changes and omissions in the form and detail thereof may be made therein without departing from the spirit and the scope of the invention.

we claim:

1. The method of transporting a first reactant, hydrogen gas, from a supply location to a second location remote from said supply location comprising the steps of:
   providing a flow path loop having a combination position and a regeneration position, remote from said combination position, said flow path loop including separate first and second legs extending between said combination and regeneration positions;
   providing a supply of hydrogen gas at said supply location external of said flow path loop comprising the step of reacting a hydrocarbon fuel to produce said hydrogen;
   conveying said supply of hydrogen gas from said supply location to said combination position of said flow path loop, including introducing said hydrogen gas into said flow path loop at a first location proximate said combination position;

providing a supply of a second reactant in said flow path loop at said regeneration position;

conveying said second reactant from said regeneration position to said combination position through said first leg of said flow path loop;

chemically combining, in a reversible exothermic reaction, said hydrogen gas with said second reactant at said combination position to produce a reaction product in gaseous form;

converting said gaseous-form reaction product to a liquid-form and conveying said liquid-form reaction product to said regeneration position through said second leg of said flow path loop;

regenerating, at said regeneration position, in a chemical reaction the reverse of said combination reaction, said hydrogen gas and said second reactant in gaseous form, said step of regenerating providing said supply of second reactant at said regeneration position;

separating, at said second location proximate said regeneration position, at least a portion of said regenerated hydrogen gas from said regenerated second reactant; and removing at least a portion of said separated hydrogen gas from said flow path loop at said second location, wherein the rate at which said hydrogen gas is introduced into said flow path loop at said first location is at least as great as the rate of removal of said hydrogen gas from said flow path loop at said second location.

2. The method according to claim 1 wherein said step of reacting a hydrocarbon fuel produces hydrogen plus other gases, and the step of conveying hydrogen into said flow path loop includes conveying said other gases into said flow path loop at said first location, and wherein the step of chemically combining includes selectively reacting said hydrogen gas with said second reactant at said combination position to produce said reaction product in gaseous form, said other gases being mixed with said gaseous reaction product, including the steps of separating said other gases from said reaction product and removing said separated other gases from said flow path loop before conveying said reaction product to said regeneration position.

3. The method according to claim 2 wherein said other gases include carbon monoxide and steam.

4. The method according to claim 1, or 2 wherein said second reactant is toluene and said reaction product is methylocyclohexane.

5. The method according to claim 1 or 2 wherein the step of separating at said second location comprises condensing at least a portion of said regenerated second reactant gas to convert it to a liquid while retaining said regenerated hydrogen gas in gaseous form.

6. The method according to claim 1 or 2 wherein said liquid-form reaction product fully occludes at least a portion of said second leg; and said regeneration reaction creates regenerated reactants at sufficient pressure relative to the pressure of said gaseous reaction product produced at said combination position to establish passive flow of first and second regenerated reactants in gaseous form from said regeneration position to said combination position and to establish passive flow of said liquid-form reaction product to said regeneration position.

* * * * *